United States Patent [19]
Peyman

[11] Patent Number: 5,855,907
[45] Date of Patent: Jan. 5, 1999

[54] METHOD OF TREATMENT OF MIGRAINE

[76] Inventor: Gholam A. Peyman, 202 Gravier, Suite B, New Orleans, La. 70112-2234

[21] Appl. No.: 828,144

[22] Filed: Mar. 24, 1997

[51] Int. Cl.$^6$ .............................. A61F 13/02; A61L 15/16
[52] U.S. Cl. .......................... 424/434; 424/443; 424/445; 424/449
[58] Field of Search ................................... 424/443, 445, 424/434, 449

[56] References Cited

U.S. PATENT DOCUMENTS 5,565,568  10/1996  Cho et al. ............................... 544/373

OTHER PUBLICATIONS

Marr, et al., *Am. J. of Opthalmology*, vol. 43, pp. 606–610, (1957).
Edvinsson, et al., "Adrenergic, cholinergic and peptidergic nerve fibres in dura matter—involvement in headache?" *Cephalagia*, vol. 1, pp. 175–179, (1981).
Barré, "Cocaine as an Abortive Agent in Cluster Headache," *Journal of Headache*, vol. 22, pp. 69–73, (1982).
Awouters, et al., "Pharmacology of Antidiarrheal Drugs" *Ann. Rev. Pharmacol Toxicol* vol. 23, pp. 279–301, (1983).
Hiner, et al., "Antimigraine Drug Interactions with 5–Hydroxytrytamine$_{1A}$Receptors" *Annals of Neurology*, vol. 19, pp. 511–513, (1986).
Waeber, et al., "GR 43175: A Preferential 5–HT$_{1D}$ Agent in Monkey and Human Brains as Shown by Autoradiography" *Synapse*, vol. 4, pp. 168–170, (1989).
Dihn, et al., "Cerebral Vasodilation after the Thermocoagulation of the Trigeminal Gaglion in Humans" *Neurosurgery*, vol. 31, No. 4, pp. 658–663, (1992).
Davidoff, "Migraine: Manifestation, Pathogenesis and Management" Published by F.A. Davis Company of Philadelphia, U.S.A., pp. 242 (1995).
Kudrow, et al., "Rapid and Sustained Relief of Migraine Attacks with Intranasal Lidocaine: Preliminary Findings," *Headache*, vol. 25, pp. 79–82, (1995).
Maizels, et al., "Intranasal Lidocaine for Treatment of Migraine" *JAMA*, vol. 276, pp. 319–321, (1996).
Diamond, et al., "Long–term Study of Proranolo in the Treatment of Migraine." *Headache*, vol. 22, pp. 268–271, (Sep. 1982).
Engelstoft, et al., "Synthesis and 5HT Modulating Activity of Stereoisomers of 3–Phenoxymethyl–4–phenylpiperidines." *Acta Chemica Scandanavica* vol. 50, pp. 164–169, (1996).
Fischer, et al., "Butorphanol (Stadol): A Study in problems of current drug information and control.", OJAAN, vol. 48, No. 5, May 1997.
Kudrow, Lee, "Natural History of Cluster headaches —Part 1 Outcome of Drop–out Patients." *Headache*, vol. 22, (Sep. 1982).
Peregaard, et al., "σ Ligands with Subnanomars Affinity and Preference for the $σ_2$ Binding Site. 1,3–(ω–Aminoalkyl) –1H–indoles." *J. Med. Chem.* vol. 38, pp. 1998–2008, (1995).
Shaw, et al., "Effects of Phenylpiperidine Opioids Antagonists on Food Consumption and Weight Gain of the Obese Zucker Rat." , *J. of Pharm. and Experimental Therapeutics*, vol. 253, No. 1, Dec. 18, 1989.
Soneson, et al., "Substituted (S)–Phenylpiperidines and Rigid Congeners as Preferential Dopamines Autoreceptor Antagonists: Synthesis and Structure–Activity Relationships." *J. Amer. Chem.*, vol. 37, pp. 2735–2753, (1994).
Sonesson, et al., "Substituted 3–Phenylpiperidines: New Centrally Acting Dopamines Autoreceptor Antagonists." *J. Amer. Chem.*, vol. 36, pp. 3188–3196, (1993).
Fisher et al., Butorphanol (stadol): A study in problems of current drug information and control, Neurology (1997), 48(5), 1156–1160.

*Primary Examiner*—Carlos A. Azpuru
*Attorney, Agent, or Firm*—Dechert Price & Rhoads

[57] ABSTRACT

The present invention relates to, among other things, methods of treatment of migraine headache in humans with reduced side effects by the topical administration of a migraine-ameliorating effective amount of an opioid, singly, or in combination with other pharmacological agents, including vasoconstrictors, antiinflammatory agents, antimicrobial agents, decongestants and non-opioid migraine drugs.

24 Claims, No Drawings

METHOD OF TREATMENT OF MIGRAINE

Migraine headaches (also referred to as "migraines") are generally described as recurrent severe headaches, and are suffered by about 70% of adult women and about 6% of adult men. Mizell et al., JAMA 276:319–321 (July 1996). They can be disabling, with each migraine lasting about 4–72 hours, often accompanied by nausea and photophobia. The headache can be unilateral or bilateral, and is not usually controllable by simple analgesic agents.

Nonpharmacological treatments include identification and avoidance of trigger factors, such as particular foods, trauma, caffeine withdrawal and stress. Current pharmacological treatments include the administration of pizotifen, beta blockers such as propranolol and valproate, or tricyclic antidepressants such as amitriptyline, dothiepin, methylsergide and flunarizine. Pizotifen inhibits 5-hydroxytryptamine ("5-HT(2)") receptor. See Davidoff, *Migraine: Manifestation, Pathogenesis, and Management* (1995) at 242; Hiner, et al., *Annals of Neurol.*, 19:511–513 (1986). Propranolol is a beta adrenol receptor antagonist and has some antagonistic properties against 5-HT(T2) receptors. Valproate inhibits neural pathways that are mediated by gamma-aminobutric acid. The most common prophylactic drug used to treat migraine is methylsergide, which acts on a number of 5-HT receptors.

For treatment of acute migraines, other nonspecific treatments are commonly used, such as the administration of analgesics and antiinflammatory drugs, including aspirin, paracetamol, naproxen, and the like. The systemic use of analgesics associated with codeine, however, promote migraine, and overuse of such analgesics causes migraines which are difficult to treat. Also, stronger analgesics which act on the central nervous system, including morphine and pethidine (meperidine) have risks of addiction and their systemic administration generally is contraindicated for treatment of migraine.

There are also specific antimigraine treatments, which include ergotamine and its related compounds, such as sumatriptan and dihydroergotamine, which are agonists of 5-HT(1B) and 5-HT(1D) receptors. Sumatriptan is administered orally, by subcutaneous injection, or as a nasal spray. Dihydroergotamine is administered intramuscularly, or as a nasal spray. These treatments are associated with the risk of coronary vasospasm.

Although the cause of migraine is not fully understood, it is believed that migraines may be related to trigeminal innervation of the cranial circulation. Davidoff at 136; Taran et al., *Neurosurgery*, 31:658–663 (1992). The pain sensitive innervation of the cranial blood vessels is derived from the first division of the trigeminal nerve and ophthalmic branch. Stimulation of trigeminal ganglion in animals and humans produces vasodilator neuropeptide calcitonin-G related peptides. Edvinsson, *Cephalalgaia*, 1:175–179 (1981). The release of such calcitonin-G related peptides can be blocked by administration of sumatriptan, which inhibits trigeminal neural firing through activation of 5-HT(1D) receptors. Davidoff at 218; Weber et al., *Synapse*, 4:168–170 (1989).

It has been previously postulated that the sphenopalatine ganglion ("SPG") is the site of cluster headache, and such headache was inhibited by transneural application of cocaine. Barr, *Journal of Headache*, 22:69–73 (1982). The SPG is located immediately posterior to and immediately above the posterior tip of the middle turbinate behind the nasal mucosa. It is postulated that SPG plays an important role in the trigeminal system because changes in cerebral blood flow can be triggered by trigeminal stimulations, which are mediated by the SPG. Kudrow et al., Headache, 35:79–82 (1995) and Mizell et al., JAMA 276: 319–321 (July 1996). It has recently been shown that rapid and sustained relief from a migraine can be provided by intranasal application of a 4% solution of lidocaine, a local anesthetic, in about 55% of patients. It is postulated that lidococaine acts on the SPG. Id.

While intranasal application of lidocaine provides relief, it also has side effects, including a burning sensation or numbness in the nose or in and around the eyes. Most seriously, it can also produce numbness in the throat, creating a sensation of gagging. If the patient eats or drinks, aspiration in the pharynx, and misdirection of the food into the lungs can readily occur, with the possible consequence of aspiration pneumonia. There is also the possibility of an allergic reaction to lidocaine and other local anesthetic agents. It is also known that repeated local administration of local anesthetic agents can be toxic to mucosal cells. Marr et al., *Am. J. of Opthalmology*, 43:706–710 (1957). There is therefore a need for an effective means of treating migraine without these side effects, which is addressed by the present invention.

SUMMARY OF THE INVENTION

The invention provides a method of treatment of migraine in humans.

The invention further provides a method of treating migraine comprising the topical administration of a migraine-ameliorating effective amount of an opioid. Preferably, the opioid is morphine or a morphine-derivative. More preferably, the opiod is loperamide hydrochloride.

In a preferred embodiment, the opioid is administered intraconjunctivally.

In another preferred embodiment, the opioid is administered transdermally.

In yet another preferred embodiment, the opioid is administered intranasally. In yet another preferred embodiment, the opioid is administered in a physiological saline solution, preferably comprising about 0.01% to about 0.5% opioid.

The invention provides methods of intranasal administration in the form of nose drops, nasal spray, gel, emulsion, and ointment. In a preferred embodiment, if the migraine is unilateral, nose drops are administered into the nostril on the same side of the head as the headache, or into both nostrils if the pain is bilateral.

The invention further provides a method of treatment of migraine comprising the topical administration of a migraine-ameliorating effective amount of an opioid in combination with a vasoconstrictor. In a preferred embodiment, the vasoconstrictor is neosynephrine.

The invention further provides a method of treatment of migraine comprising the topical administration of a migraine-ameliorating effective amount of an opioid in combination with an antiinflammatory compound.

The invention further provides a method of treatment of migraine comprising the topical administration of a migraine-ameliorating effective amount of an opioid in combination with an antiinflammatory compound which is a steroid. Preferrably, the steriod is glucocorticoid.

The invention further provides a method of treatment of migraine comprising the topical administration of a migraine-ameliorating effective amount of an opioid in combination with an antiinflammatory compound which is nonsteroidal. Preferrably, the non-steroidal antiinflammatory compound is ketorolac tromethamine or diclofenac sodium.

The invention further provides a method of treatment of migraine comprising the topical administration of a migraine-ameliorating effective amount of an opioid in combination with an antibiotic.

The invention further provides a method of treatment of migraine comprising the topical administration of a migraine-ameliorating effective amount of an opioid in combination with a non-opioid antimigraine drug. Preferrably, the non-opiod antimigraine drug is sumatriptan.

The invention further provides a method of treatment of migraine comprising the topical administration of a migraine-ameliorating effective amount of an opioid in combination with a decongestant.

Preferably, any other drug administered in combination with the opioid is administered simultaneously or sequentially with the opioid by a clinically effective means.

Further objects and advantages of the present invention will be clear from the description that follows.

DEFINITIONS

The following terms shall have the meaning set forth below:

Agonist—A chemical substance capable of combining with a nerve receptor and initiating a reaction.

Analgesic—A chemical substance capable of causing diminished sensibility to pain.

Antagonist—A chemical substance capable of inhibiting the action of an agonist.

Antiinflammatory agent—A chemical substance capable of ameliorating inflammation.

Antimicrobial agent—A substance produced by or a semisynthetic substance derived from a microorganism and able in dilute solution to inhibit or kill another microorganism, including bacteria, fungi, viruses and the like.

Migraine—A medical condition marked by severe headache, often recurrent, and often accompanied by nausea and vomiting.

Opiold—A natural or synthetic chemical substance which is opium- or morphine-like in its analgesic properties; that is, a substance capable of acting as an analgesic, for example, by interacting with an opioid receptor.

Systemic—Of or relating to the entire organism.

Topical—Of or relating to external local area(s) of the human body, including, but not limited to, the skin, the nasal mucosa and the conjunctiva.

Vasoconstrictor—A chemical substance that induces the narrowing of the lumen of blood vessels.

DETAILED DESCRIPTION

The present invention is directed, among other things, to methods of treating migraine by the topical administration of a migraine-ameliorating effective amount of an opioid.

Opioids include opium derivatives such as phenanthrenes (including morphine, codeine and thebaine) and benzylisoquinolines (such as papaverine and noscapine); semisynthetic derivatives, such as apomorphine, diacetylmorphine, hydromorphone, and the like; non-opium derivatives with actions similar to morphine, including morphinans, benzomorphans, methadones, phenylpiperidines, and proprionanilides; and synthetic compounds with opium-like or morphine-like actions, including pentazocine, butorphanol, buprenorphine, meptazinol, and the like. Preferably, the opioid is morphine, or a derivative thereof, semisynthetic or otherwise. In a preferred embodiment, the opioid is loperamide hydrochloride, a phenylpiperidine.

It should be understood that "a migraine-ameliorating effective amount" refers to an amount of opioid which effects a prophylactic or therapeutic response in the patient in need of such a response over a reasonable time frame, causing either a diminution or an eradication of one or more of the symptoms of migraine. While the precise mechanism by which the topical administration of a migraine-ameliorating effective amount of an opioid relieves migraine is unknown, without limiting the invention to any particular theory, it is believed that the treatment is effective because the opioid affects the sphenopalatine ganglion ("SPG"). It is thus readily apparent to one skilled in the art that the effectiveness of topical application is correlated with maximizing the degree to which the opioid is absorbed and affects the SPG, and minimizing the degree to which the opioid is absorbed systemically. Thus, topical administration on and around the sinal cavity is preferred, including the administration of the opioid conjunctivally, intranasally, or transdermally in the region of the sinal cavity.

Administration of "an opioid" should be understood to refer to the administration of any opioid or combination of opioids.

Administration "conjunctivally" should be understood to mean administration to the conjunctiva, that is, the mucosa lining the eyelids. Administration "intranasally" should be understood to mean administration to the nasal mucosa. Administration "transdermally" should be understood to mean administration to the skin in a preparation which penetrates the skin, at least partially.

An advantage of such topical administration is the effectiveness of low concentrations of opioids, reducing any central nervous system effect even if fully absorbed systemically. A further advantage of such topical administration is low absorption through a systemic route, reducing systemic side effects.

An advantage of the administration of opioids is the elimination of side effects such as burning or numbness in the nose and throat caused by the administration of local anesthetics. A further advantage is the elimination of allergic reactions to local anesthetics. A further advantage is the lowered risk of toxicity to mucosal cells known to be caused by the repeated application of local anesthetic agents.

Preferably, the opioid is administered intranasally and is absorbed through the nasal mucosa.

One skilled in the art will appreciate that suitable methods of administering an opioid intranasally are available, and, although more than one route can be used to administer a particular compound, a particular route can provide a more immediate and more effective reaction than another route. Pharmaceutically acceptable excipients are also well-known to those who are skilled in the art, and are readily available. The choice of excipient will be determined in part by the particular opioid, as well as by the particular method used to administer the composition. Accordingly, there is a wide variety of suitable formulations of the pharmaceutical composition identified in the context of the present invention. The following methods and excipients are merely exemplary and are in no way limiting.

Formulations suitable for intranasal administration can consist of (a) liquid solutions, such as a migraine-ameliorating effective amount of the agent dissolved in diluents, such as water, or saline; (b) suspensions in an appropriate liquid; and (c) suitable emulsions, all of which can be administered in suitable ways, including nose drops and nasal sprays. Formulations can also include gels, ointments and the like, containing, in addition to the active ingredient, such excipients as are known in the art, all of which can be administered in suitable ways, including by painting on the nasal mucosa, or squirting into the nose.

The opioid, alone or in combination with other suitable components, can also be made into aerosol formulations to be administered via a nasal spray or nasal inhalation. These aerosol formulations can be placed into pressurized acceptable propellants, such as dichlorodifluoromethane, propane, nitrogen, and the like. They may also be formulated as pharmaceuticals for non-pressured preparations such as in a nebulizer or an atomizer.

Preferably, the opioid is administered intranasally in liquid form, most preferably in a physiological saline solution. In a preferred embodiment, the solution is administered as nose drops. In another preferred embodiment, the opioid in liquid form is administered as a nasal spray.

The dose administered in the context of the present invention should be a migraine-ameliorating effective amount of opioid. One skilled in the art will recognize that dosage will depend upon a variety of factors, including the strength of the particular compound employed, the condition of the patient, the body weight of the patient, as well as the severity of the migraine. The size of the dose will also be determined by the existence, nature, and extent of any adverse side-effects that might accompany the administration of a particular compound. The preferred dosage is the amount that results in signification elimination or eradication of symptoms, without significant side effects. Given these parameters, the unit dosage can range from about 0.1 mg/ml to about 10 mg/ml.

In a preferred embodiment, the opioid is administered as a solution comprising about 0.01% to about 0.5% opioid, although each opiate compound may have its particular optimal concentration, which can be readily determined by one skilled in the art. More preferably, the solution is a physiological saline solution. Preferably, the amount of solution administered is about 0.01 ml to about 5 ml. More preferably, the amount of solution is about 0.5 ml.

Preferably, the symptoms are relieved within about 5 to about 120 minutes after administration of a dose of opioid, and more preferably within about 5 to about 10 minutes, and if they are not relieved within about 5 to about 120 minutes, a second dose can be administered.

The methods of the invention further include a method of treatment of migraine comprising the topical administration of a migraine-ameliorating effective amount of an opioid, in combination the administration of a vasoconstrictor, both according to the parameters discussed above. An advantage of such a method is the enhanced opening of the nasal passages by the vasoconstrictor, such as neosynephrine, and the like.

The methods of the invention further include a method of treatment of migraine comprising the topical administration of an opioid, in combination with the administration of an antiinflammatory compound. Antiinflammatory compounds include steroids, particularly glucocorticoids, for example, cortisol, cortisone, prednisolone, dexamethasone and the like; and nonsteroids, particularly salicylates (such as aspirin), pyrazolon derivatives (such as phenylbutazone), indomethacin and sulindac, fenamates, and propionic acid derivatives (such as ibuprofen). In a preferred embodiment, the nonsteroidal antiinflammatory agent ketorolac tromethamine in a 0.5% solution or diclofenac sodium in a 0.1% solution is administered.

The methods of the invention further include a method of treatment of migraine comprising the topical administration of an opioid in combination with the administration of an antimicrobial agent, such as neosporin, cortisporin, and the like. Preferably, the antimicrobial agent is neosporin. An advantage of such a method is the treatment of any local infection.

The methods of the invention further include a method of treatment of migraine comprising the topical administration of an opioid in combination with the administration of a non-opiate antimigraine drug, such as pizotifen, propranolol, valproate, amitriptyline, dothiepin, methylsergide, sumatriptan or flunarizine. Preferably, the non-opiate antimigraine drug is sumatriptan.

The methods of the invention further include a method of treatment of migraine comprising the topical administration of an opioid in combination with the administration of a decongestant. An advantage of such method is the enhanced opening of the nasal passages.

The administration of another drug "in combination with" an opioid refers to the administration of the other drug either simultaneously or sequentially with the opioid. The suitability of administration of a particular compound of the classes discussed above in combination with an opiate compound, its method of administration, dosage, and timing of administration will be apparent to one skilled in the art dependent on the patient and the nature and severity of symptoms.

The following example further illustrates the present invention but, of course, should not be construed as in any way limiting its scope.

EXAMPLE 1

This example illustrates a method of administering a migraine-ameliorating amount of an opioid intranasally.

The patient lies supine with the head hyperextended 45 degrees while rotated 30 degrees to the side of the headache. 0.5 ml of an 0.025% opiate solution is dripped into the nostril on the same side as the headache over a period of 30 to 60 seconds. If the headache is bilateral, the solution is administered to both nostrils. If the symptoms are not relieved within 5 to 10 minutes, a second dose is administered.

What is claimed:

1. A method of treating a migraine headache comprising the topical administration of a migraine-ameliorating effective amount of loperamide hydrochloride.

2. The method of claim 1 in which the loperamide hydrochloride is administered intraconjunctivally.

3. The method of claim 1 in which the loperamide hydrochloride is administered transdermally.

4. The method of claim 1 in which the loperamide hydrochloride is administered intranasally.

5. The method of claim 4 in which the loperamide hydrochloride is administered in the form of nose drops.

6. A method of treating a migraine headache comprising the topical administration of a migraine-amelioratinz effective amount of an opioid in which the migraine comprises a unilateral headache and the nose drops are administered to the nostril on the same side as the headache.

7. The method of claim 4 in which the loperamide hydrochloride is administered in the form of a nasal spray.

8. The method of claim 4 in which the loperamide hydrochloride is administered in the form of a gel, emulsion or ointment.

9. The method of claim 1 in which the loperamide hydrochloride is administered in a physiological saline solution.

10. The method of claim 9 in which the concentration of loperamide hydrochloride in the saline solution is about 0.01% to about 0.5% loperamide hydrochloride.

11. The method of claim 1 in which the loperamide hydrocloride is administered in combination with a vasoconstrictor.

12. The method of claim 11 in which the vasoconstrictor is neosynephrine.

13. The method of claim 1 in which the loperamide hydrochloride is administered in combination with an antiinflammatory agent.

14. The method of claim 13 in which the antiinflammatory agent is a steroid.

15. The method of claim 14 in which the antiinflammatory agent is a glucocorticoid.

16. The method of claim 13 in which the antiinflammatory agent is nonsteroidal.

17. The method of claim 16 in which the antiinflammatory agent is ketorolac tromethamine or diclofenac sodium.

18. The method of claim 1 in which the loperamide hydrochloride is administered in combination with an antimicrobial agent.

19. The method of claim 18 in which the antimicrobial agent is neosporin.

20. The method of claim 1 in which the loperamide hydrochloride is administered in combination with a non-opioid antimigraine drug.

21. The method of claim 20 in which the antimigraine drug is sumatriptan.

22. The method of claim 1 in which the loperamide hydrochloride is administered in combination with a decongestant.

23. A pharmaceutical composition adapted for topical delivery comprising loperamide hydrochloride in a physiologic saline solution effective for treating migraine headache.

24. The pharmaceutical composition of claim 23 in unit dosage form.

* * * * *